(12) United States Patent
Cowles et al.

(10) Patent No.: US 10,656,024 B2
(45) Date of Patent: May 19, 2020

(54) MOLTEN MATERIAL THERMOCOUPLE METHODS AND APPARATUS

(71) Applicant: Corning Incorporated, Corning, NY (US)

(72) Inventors: Curtis Richard Cowles, Corning, NY (US); Gilbert De Angelis, Lindley, NY (US); Jeffrey Lee Merriman, Wellsboro, PA (US); Katherine Rose Rossington, Corning, NY (US); Michael Joshua Snyder, Almond, NY (US)

(73) Assignee: Corning Incorporated, Corning, NY (US)

( * ) Notice: Subject to any disclaimer, the term of this patent is extended or adjusted under 35 U.S.C. 154(b) by 617 days.

(21) Appl. No.: 15/091,183

(22) Filed: Apr. 5, 2016

(65) Prior Publication Data

US 2017/0284872 A1     Oct. 5, 2017

(51) Int. Cl.
*G01K 7/02*     (2006.01)
*G01N 33/38*     (2006.01)
(Continued)

(52) U.S. Cl.
CPC ............ *G01K 7/02* (2013.01); *C03B 5/167* (2013.01); *C03B 5/1672* (2013.01);
(Continued)

(58) Field of Classification Search
CPC ..... C03B 5/167; C03B 5/1672; C03B 5/1675; C03B 2211/70; G01K 7/02; G01K 1/08;
(Continued)

(56) References Cited

U.S. PATENT DOCUMENTS 3,329,534 A     7/1967     Adler et al.
5,181,779 A *   1/1993     Shia ..................... G01K 1/105
                                                          136/232
(Continued)

FOREIGN PATENT DOCUMENTS

CN     1936527 A     3/2007
CN     202188921 U   4/2012
(Continued)

OTHER PUBLICATIONS

Full english translation of prior art document to Asano JP 06-329420 A that was cited in the last office action dated Aug. 6, 2019 (Year: 1994).*
(Continued)

*Primary Examiner* — Peter J Macchiarolo
*Assistant Examiner* — John M Royston
(74) *Attorney, Agent, or Firm* — Matthew B. McNutt; Ryan T. Hardee (57) ABSTRACT

A molten material apparatus can include a container including a wall at least partially defining a containment area and an opening extending through the wall. The molten material apparatus can include a protective sleeve mounted at least partially within the opening of the wall of the container. A thermocouple can be positioned within an internal bore of the protective sleeve. A method of processing molten material can include inserting a thermocouple into a protective sleeve fabricated from a refractory ceramic material, and measuring a temperature of material within a containment area of a container with the thermocouple.

25 Claims, 5 Drawing Sheets

(51) Int. Cl.
  *G01K 1/08* (2006.01)
  *H01L 35/32* (2006.01)
  *H01L 35/20* (2006.01)
  *G01N 33/205* (2019.01)
  *C03B 5/167* (2006.01)
  *F27D 1/00* (2006.01)
  *F27B 3/28* (2006.01)
  *F27D 21/00* (2006.01)

(52) U.S. Cl.
  CPC .............. *C03B 5/1675* (2013.01); *F27B 3/28* (2013.01); *F27D 21/0014* (2013.01); *G01K 1/08* (2013.01); *G01N 33/205* (2019.01); *G01N 33/386* (2013.01); *H01L 35/20* (2013.01); *H01L 35/32* (2013.01); *C03B 2211/70* (2013.01)

(58) Field of Classification Search
  CPC ................ G01N 33/205; G01N 33/386; F27D 21/0014; F27B 3/28; H01L 35/20; H01L 35/32
  See application file for complete search history.

(56) References Cited

U.S. PATENT DOCUMENTS

| | | | |
|---|---|---|---|
| 5,197,805 A | 3/1993 | Wilson | |
| 6,701,751 B2 | 3/2004 | Arechaga et al. | |
| 8,530,804 B2 | 9/2013 | Kolberg et al. | |
| 2003/0180537 A1* | 9/2003 | Meyer | B01D 39/06 428/404 |
| 2004/0135379 A1* | 7/2004 | Meier | B01J 3/03 292/256.5 |
| 2009/0052498 A1 | 2/2009 | Halpin et al. | |
| 2011/0150034 A1 | 6/2011 | Breimon | |
| 2012/0106594 A1* | 5/2012 | Boudreault | G01K 7/04 374/179 |
| 2013/0283861 A1* | 10/2013 | Mobley | C03B 5/167 65/135.1 |

FOREIGN PATENT DOCUMENTS

| | | | |
|---|---|---|---|
| CN | 202533192 U | 11/2012 | |
| CN | 102889941 A | 1/2013 | |
| CN | 203908697 U | 10/2014 | |
| GB | 719026 A | 11/1954 | |
| JP | 06329420 A * | 11/1994 | .......... C03B 5/0336 |
| JP | 2000213997 A * | 8/2000 | |
| JP | 2006153706 A | 6/2006 | |
| WO | 2015110986 A1 | 7/2015 | |

OTHER PUBLICATIONS

International Search Report of the International Searching Authority; PCT/US2017/025874; dated June 23, 2017; 11 Pages; European Patent Office.

* cited by examiner

FIG. 7 ns and apparatus for measuring a temperature of a material with a thermocouple and, more particularly, to methods and apparatus for measuring a temperature of molten glass-forming material within a container with a thermocouple positioned in a protective sleeve.

MOLTEN MATERIAL THERMOCOUPLE METHODS AND APPARATUS

FIELD

The present disclosure relates generally to methods and apparatus for measuring a temperature of a material with a thermocouple and, more particularly, to methods and apparatus for measuring a temperature of molten glass-forming material within a container with a thermocouple positioned in a protective sleeve.

BACKGROUND

It is known to measure a temperature with a thermocouple. It is further known to place a thermocouple in a protective sleeve to protect the thermocouple.

SUMMARY

The following presents a simplified summary of the disclosure in order to provide a basic understanding of some exemplary embodiments described in the detailed description.

In one embodiment, a molten material apparatus can include a container including a wall at least partially defining a containment area and an opening extending through the wall. The molten material apparatus can include a protective sleeve mounted at least partially within the opening of the wall of the container. The protective sleeve can include a first end portion, a second end portion opposite the first end portion, and an internal bore. The internal bore of the protective sleeve can include an open end at the first end portion and a closed end at the second end portion. The closed end can be defined by an inner end surface of the second end portion of the protective sleeve. The molten material apparatus can include a thermocouple positioned within the internal bore of the protective sleeve. The thermocouple can be biased towards the inner end surface of the second end portion of the protective sleeve.

In another embodiment, the thermocouple can contact the inner end surface of the second end portion of the protective sleeve.

In another embodiment, the molten material apparatus can include a support sleeve at least partially positioned within the internal bore of the protective sleeve. The support sleeve can include a first end portion, a second end portion opposite the first end portion of the support sleeve, and an internal bore. The internal bore of the support sleeve can include an open end at the first end portion of the support sleeve.

In another embodiment, the internal bore of the support sleeve can include a closed end at the second end portion of the support sleeve. The closed end can be defined by an inner end surface of the second end portion of the support sleeve. The thermocouple can be positioned within the internal bore of the support sleeve. The thermocouple can be biased against the inner end surface of the second end portion of the support sleeve.

In another embodiment, an outer end surface of the second end portion of the support sleeve can be biased against the inner end surface of the second end portion of the protective sleeve.

In another embodiment, the protective sleeve can be fabricated from a refractory ceramic material.

In another embodiment, the refractory ceramic material can include a chemical compound selected from the group consisting of tin oxide, chrome oxide, and fused zirconia.

In another embodiment, the thermocouple can include a platinum/rhodium alloy thermocouple.

In another embodiment, the thermocouple can include a type B thermocouple.

In another embodiment, the support sleeve can include a platinum or a platinum alloy.

In another embodiment, the protective sleeve can extend within the containment area by a distance of from greater than 0 cm to about 25 cm from an inner surface of the wall of the container.

In another embodiment, the molten material apparatus can include molten glass-forming material within the containment area of the container.

In another embodiment, the molten glass-forming material includes a metal.

In another embodiment, the molten material apparatus can include a layer of solid glass lining an inner surface of the wall of the container.

In another embodiment, solid glass can seal an interface between the wall of the container and the protective sleeve.

In another embodiment, a molten material apparatus can include a container including a wall at least partially defining a containment area and an opening extending through the wall. The molten material apparatus can include a protective sleeve mounted at least partially within the opening of the wall of the container. The protective sleeve can be fabricated from a refractory ceramic material that includes a chemical compound selected from the group consisting of tin oxide, chrome oxide, and fused zirconia. The molten material apparatus can include a thermocouple positioned within an internal bore of the protective sleeve.

In another embodiment, the thermocouple can contact an inner end surface of the protective sleeve that at least partially defines the internal bore of the protective sleeve.

In another embodiment, the molten material apparatus can include a support sleeve at least partially positioned within the internal bore of the protective sleeve.

In another embodiment, the thermocouple can be positioned within an internal bore of the support sleeve.

In another embodiment, the thermocouple can contact an inner end surface of the support sleeve that defines a closed end of the internal bore of the support sleeve, and an outer end surface of the support sleeve can contact an inner end surface of the protective sleeve that at least partially defines the internal bore of the protective sleeve.

In another embodiment, a method of processing molten material can include inserting a thermocouple into a protective sleeve fabricated from a refractory ceramic material. The protective sleeve can be mounted at least partially within an opening of a wall of a container, and the method can include measuring a temperature of material within a containment area of the container with the thermocouple.

In another embodiment, the method can include solidifying a quantity of the molten glass-forming material into a layer of solid glass lining an inner surface of the wall of the container by cooling the wall of the container with liquid.

In another embodiment, an end of the protective sleeve can pass through the opening of the wall and through the layer of solid glass such that an end of the protective sleeve is positioned within the molten glass-forming material.

In another embodiment, the method can include solidifying a quantity of the molten glass-forming material into a solid glass that seals an interface between the wall of the container and the protective sleeve.

In another embodiment, measuring the temperature of material can include biasing the thermocouple against an inner end surface of the protective sleeve defining a closed end of an internal bore of the protective sleeve.

In another embodiment, the method can include supporting the protective sleeve by inserting a support sleeve at least partially within an internal bore of the protective sleeve.

In another embodiment, measuring the temperature of the material can include biasing the thermocouple against an inner end surface of a closed end portion of the support sleeve such that an outer end surface of the closed end portion of the support sleeve is biased against an inner end surface of the protective sleeve defining a closed end of the internal bore of the protective sleeve.

It is to be understood that both the foregoing general description and the following detailed description present embodiments of the present disclosure, and are intended to provide an overview or framework for understanding the nature and character of the embodiments as they are described and claimed. The accompanying drawings are included to provide a further understanding of the embodiments, and are incorporated into and constitute a part of this specification. The drawings illustrate various embodiments of the disclosure, and together with the description, serve to explain the principles and operations thereof.

BRIEF DESCRIPTION OF THE DRAWINGS

These and other features, embodiments, and advantages of the present disclosure can be further understood when read with reference to the accompanying drawings.

DETAILED DESCRIPTION

Apparatus and methods will now be described more fully hereinafter with reference to the accompanying drawings in which exemplary embodiments of the disclosure are shown. Whenever possible, the same reference numerals are used throughout the drawings to refer to the same or like parts. However, this disclosure may be embodied in many different forms and should not be construed as limited to the embodiments set forth herein.

Glass sheets are commonly fabricated by flowing molten glass to a forming body whereby a glass ribbon may be formed by a variety of ribbon forming processes including, float, slot draw, down-draw, fusion down-draw, up-draw, press roll or any other forming processes. The glass ribbon from any of these processes may then be subsequently divided to provide one or more glass sheets suitable for further processing into a desired application, including but not limited to, a display application. For example, the one or more glass sheets can be used in a variety of display applications, including liquid crystal displays (LCDs), electrophoretic displays (EPD), organic light emitting diode displays (OLEDs), plasma display panels (PDPs), or the like.

Figure 1:
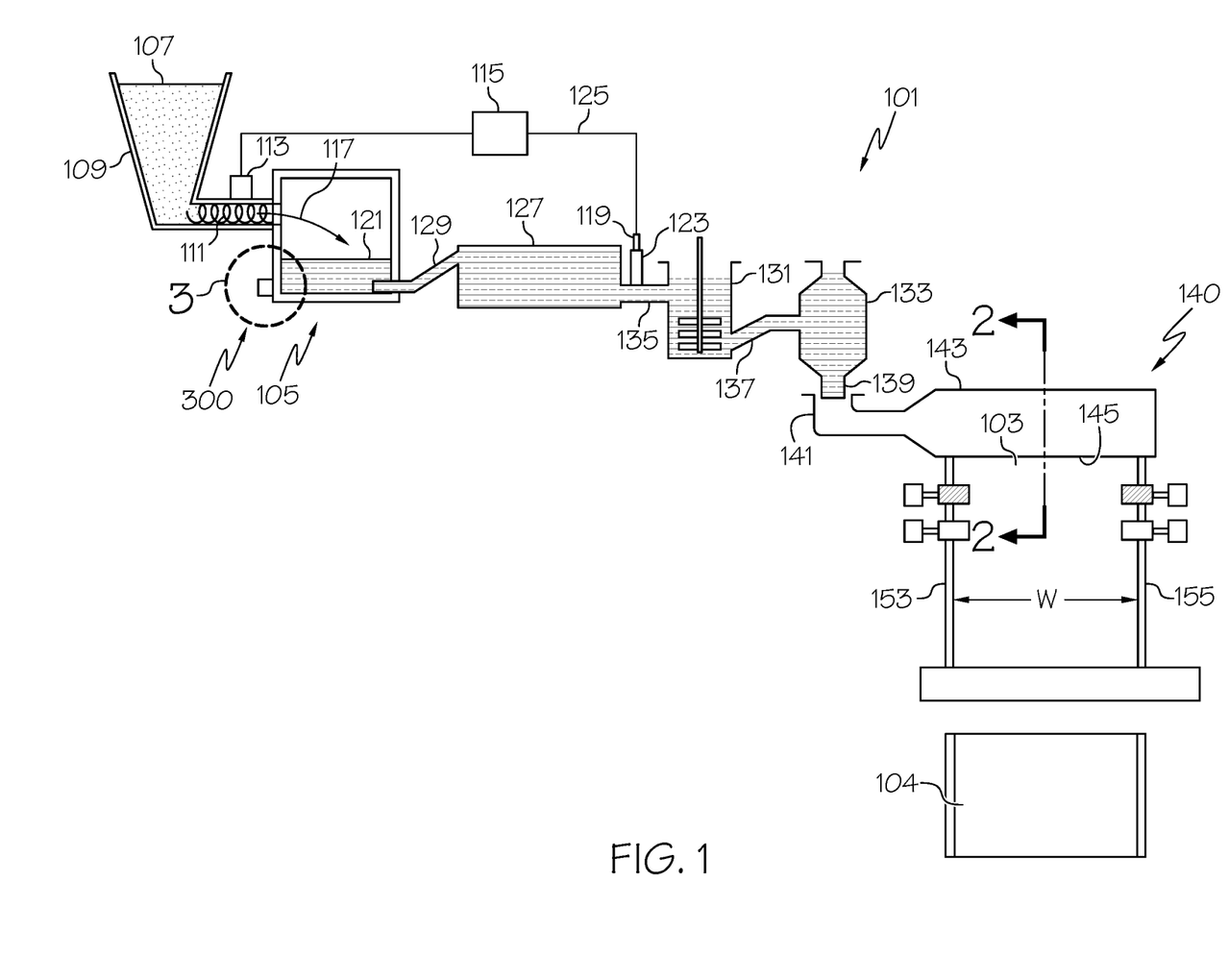
FIG. 1 illustrates a schematic view of a glass manufacturing apparatus in accordance with embodiments disclosed herein.

FIG. 1 schematically illustrates an exemplary glass manufacturing apparatus 101 to form a glass ribbon 103. For illustration purposes, the glass manufacturing apparatus 101 is illustrated as a fusion down-draw apparatus, although other glass manufacturing apparatus for up-draw, float, press rolling, slot draw, etc. may be provided in further embodiments. As illustrated, the glass manufacturing apparatus 101 can include a melting vessel 105 oriented to receive batch material 107 from a storage bin 109. The batch material 107 can be introduced by a batch delivery device 111 powered by a motor 113. An optional controller 115 can be operated to activate the motor 113 to introduce a desired amount of batch material 107 into the melting vessel 105, as indicated by arrow 117. A glass melt probe 119 can be used to measure a level of molten material 121 within a standpipe 123 and communicate the measured information to the controller 115 by way of a communication line 125.

The glass manufacturing apparatus 101 can also include a fining vessel 127 located downstream from the melting vessel 105 and coupled to the melting vessel 105 by way of a first connecting conduit 129. In some embodiments, molten material 121 may be gravity fed from the melting vessel 105 to the fining vessel 127 by way of the first connecting conduit 129. For example, gravity may act to drive the molten material 121 to pass through an interior pathway of the first connecting conduit 129 from the melting vessel 105 to the fining vessel 127. Within the fining vessel 127, bubbles may be removed from the molten material 121 by various techniques.

The glass manufacturing apparatus 101 can further include a mixing chamber 131 that may be located downstream from the fining vessel 127. The mixing chamber 131 can be used to provide a homogenous composition of molten material 121, thereby reducing or eliminating cords of inhomogeneity that may otherwise exist within the molten material 121 exiting the fining vessel 127. As shown, the fining vessel 127 may be coupled to the mixing chamber 131 by way of a second connecting conduit 135. In some embodiments, molten material 121 may be gravity fed from the fining vessel 127 to the mixing chamber 131 by way of the second connecting conduit 135. For instance, gravity may drive the molten material 121 to pass through an interior pathway of the second connecting conduit 135 from the fining vessel 127 to the mixing chamber 131.

The glass manufacturing apparatus 101 can further include a delivery vessel 133 that may be located downstream from the mixing chamber 131. The delivery vessel 133 can condition the molten material 121 to be fed into a glass former 140. For example, the delivery vessel 133 can function as an accumulator and/or flow controller to adjust and provide a consistent flow of molten material 121 to the glass former 140. As shown, the mixing chamber 131 may be coupled to the delivery vessel 133 by way of a third connecting conduit 137. In some embodiments, molten material 121 may be gravity fed from the mixing chamber 131 to the delivery vessel 133 by way of the third connecting conduit 137. For instance, gravity may drive the molten material 121 to pass through an interior pathway of the third connecting conduit 137 from the mixing chamber 131 to the delivery vessel 133.

As further illustrated, a delivery pipe 139 can be positioned to deliver molten material 121 to the glass former 140 of the glass manufacturing apparatus 101. The glass former 140 may draw the molten material 121 into the glass ribbon 103 off of a root 145 of a forming vessel 143. In the illustrated embodiment, the forming vessel 143 can be provided with an inlet 141 oriented to receive molten material 121 from the delivery pipe 139 of the delivery vessel 133. A width "W" of the glass ribbon 103 can extend between a first vertical edge 153 of the glass ribbon 103 and a second vertical edge 155 of the glass ribbon 103.

Figure 2:
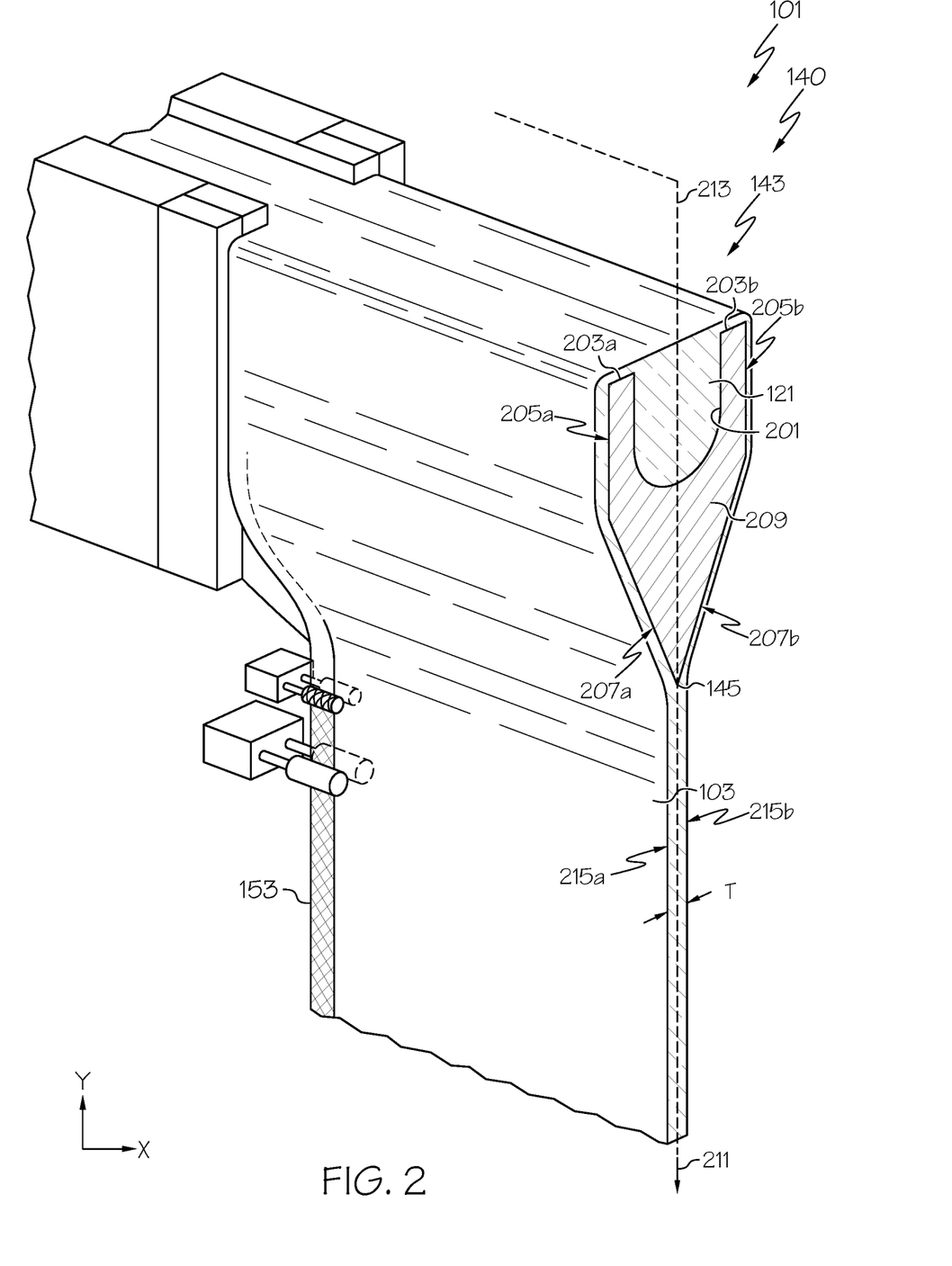
FIG. 2 illustrates a cross-sectional perspective view of the glass manufacturing apparatus along line 2-2 of FIG. 1.

FIG. 2 is a cross-sectional perspective view of the glass manufacturing apparatus 101 along line 2-2 of FIG. 1. As shown, the forming vessel 143 can include a trough 201 oriented to receive the molten material 121 from the inlet 141. The forming vessel 143 can further include a forming wedge 209 including a pair of downwardly inclined converging surface portions 207a, 207b extending between opposed ends of the forming wedge 209. The pair of downwardly inclined converging surface portions 207a, 207b converge along a draw direction 211 to form the root 145. A draw plane 213 extends through the root 145 wherein the glass ribbon 103 may be drawn in the draw direction 211 along the draw plane 213. As shown, the draw plane 213 can bisect the root 145 although the draw plane 213 may extend at other orientations relative to the root 145.

Referring to FIG. 2, in one embodiment, the molten material 121 can flow from the inlet 141 into the trough 201 of the forming vessel 143. The molten material 121 can then overflow from the trough 201 by simultaneously flowing over corresponding weirs 203a, 203b and downward over the outer surfaces 205a, 205b of the corresponding weirs 203a, 203b. Respective streams of molten material 121 then flow along the downwardly inclined converging surface portions 207a, 207b of the forming wedge 209 to be drawn off the root 145 of the forming vessel 143, where the flows converge and fuse into the glass ribbon 103. The glass ribbon 103 may then be fusion drawn off the root 145 in the draw plane 213 along draw direction 211 where a glass sheet 104 (see FIG. 1) may then be subsequently separated from the glass ribbon 103.

As shown in FIG. 2, the glass ribbon 103 may be drawn from the root 145 with a first major surface 215a of the glass ribbon 103 and a second major surface 215b of the glass ribbon 103 facing opposite directions and defining a thickness "T" of the glass ribbon 103 that can be less than or equal to about 1 millimeter (mm), less than or equal to about 0.5 millimeters, less than or equal to about 500 micrometers (μm), such as less than or equal to about 300 micrometers, such as less than or equal to about 200 micrometers, or such as less than or equal to about 100 micrometers, although other thicknesses may be provided in further embodiments. In addition, the glass ribbon 103 can include a variety of compositions including but not limited to soda-lime glass, borosilicate glass, alumino-borosilicate glass, an alkali-containing glass, or an alkali-free glass.

FIGS. 3-7 schematically illustrate features of a molten material apparatus 300 and methods of processing molten material in accordance with embodiments disclosed herein. In some embodiments, a method of processing molten material can include measuring a temperature of a material with a thermocouple 350 as well as measuring a temperature of molten glass-forming material 306 within a container 305 with a thermocouple 350 positioned in a protective sleeve 320. In some embodiments, the molten glass-forming material 306 can be provided in a container 305 (e.g., melting vessel 105, fining vessel 127, mixing chamber 131, delivery vessel 133, forming vessel 143, etc.) of a glass manufacturing apparatus (e.g., glass manufacturing apparatus 101). It is to be understood that specific embodiments disclosed herein are intended to be exemplary and therefore non-limiting.

Figure 3:
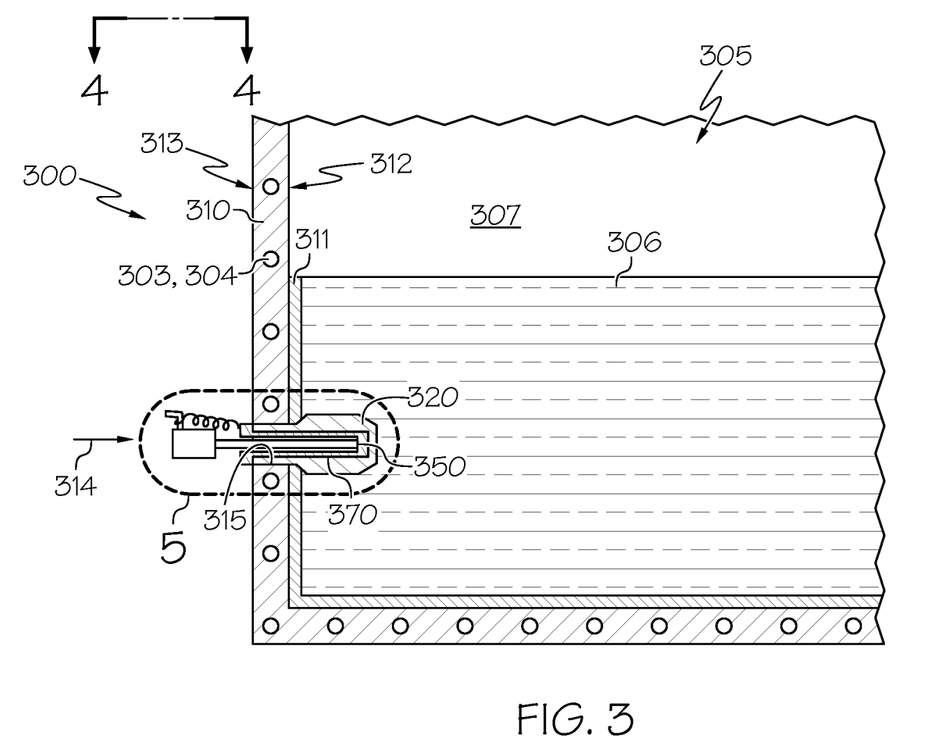
FIG. 3 illustrates an enlarged cross-sectional view of an exemplary molten material apparatus according to view 3 of FIG. 1.

As shown in FIG. 3, in one embodiment, the molten material apparatus 300 can include a container 305 including a wall 310 at least partially defining a containment area 307 and an opening 315 extending through the wall 310. The wall 310 is illustrated as an upstream end wall although the wall with the opening can be a downstream end wall, a sidewall or a bottom wall in further embodiments. Moreover, in examples where the molten material does not include a free surface, the wall may comprise the top wall in further embodiments.

The opening 315 can provide access into the containment area 307 of the container 305. As shown a single opening 315 is provided through a single wall of the container 305. In further embodiments, a plurality or all of the walls of the container may be provided with a single opening or a plurality of openings. In such embodiments, each opening or a subset of openings may be provided with a thermocouple 350 to measure a temperature associated with the location of the corresponding opening.

In some embodiments, the container 305 can be employed to contain a material in a submerged combustion melting process. A submerged combustion melting process can include applications where a fuel and an oxidant are mixed with the material (e.g., batch material 107) in the containment area 307 of the container 305 and are burned directly with the material to melt the material and form, for example, molten material 121. Submerged combustion melting of a material can cause convective stirring (e.g., agitation) of the molten material within the containment area 307 of the container 305 and can subject the container 305 and associated components to high temperatures as well as potentially corrosive environments.

In one embodiment, the molten material apparatus 300 can include molten glass-forming material 306 within the containment area 307 of the container 305. In some examples, the molten glass-forming material 306 can be cooled to form a glass, a glass-ceramic, or other material containing glass. In another embodiment, the molten glass-forming material 306 can include a metal. For instance, in one embodiment, molten glass-forming material 306 that includes metal (e.g., 30% metal by weight) that can be employed to produce a glass, glass-ceramic or other metal-containing glass that provides antimicrobial properties. In some embodiments, the molten glass-forming material 306 including metal may produce a corrosive environment within the containment area 307 of the container 305. In some examples a single metal may be provide or a combination of two or more different types of metal may be provided. While a wide range of metals are contemplated, in some embodiments, the glass-forming material 306 can include at least one metal (i.e., either alone or in any combination with any plurality of metals) selected from a group consisting of: copper, iron, silver and platinum. In one embodiment, molten glass-forming material 306 that includes copper (e.g., 30% copper by weight) that can be employed to produce a glass, glass-ceramic or other copper-containing glass that provides antimicrobial properties. In some embodiments, the molten glass-forming material 306 including copper may produce a corrosive environment within the containment area 307 of the container 305. Provisions may be made to accommodate the corrosive environment associated with the glass-forming material 306. For example, the wall of the container and other components interacting with the molten-glass forming material may be designed, as discussed below, to withstand the corrosive environment to prevent failure of the components and/or increase the life of the components.

In some embodiments, the container 305 can include a water-cooled container (e.g., melting vessel) where liquid 303 can circulate through one or more internal liquid paths 304 within the wall 310 (e.g. between an inner surface 312 of the wall 310 and an outer surface 313 of the wall 310). The liquid 303 circulating through the one or more internal liquid paths 304 within the wall 310 can reduce a temperature of the wall 310 and, therefore, extend an operating life of the container 305. In other embodiments, the molten material apparatus 300 can include a layer of solid glass 311 lining the inner surface 312 of the wall 310 of the container 305. For example, based at least in part on the reduced temperature of the wall 310 from the liquid 303 circulating through the one or more internal liquid paths 304 within the wall 310, the molten glass-forming material 306 can cool and solidify adjacent to the inner surface 312 of the wall 310 to form a layer of solid glass 311 lining the inner surface 312 of the wall 310. The layer of solid glass 311 can help prevent corrosive attack that may otherwise occur with corrosive high-temperature molten-glass forming material flowing against the inner surface 312 of the wall 310.

In some embodiments, the wall 310 of the container 305 can include a structural metal layer (e.g., steel) that can include the one or more internal liquid paths 304 through which the liquid 303 can circulate to cool the wall 310. In other embodiments, the inner surface 312 of the wall 310 can include a layer of protective metal (e.g., platinum, alumina, quartz, etc.) to separate the structural metal from the molten glass-forming material 306. The layer of solid glass 311 can line the inner surface 312 of the layer of protective metal to further separate the structural metal from the molten glass-forming material 306. Based at least in part on the corrosive nature of the molten glass-forming material 306, in some embodiments, it can be difficult to measure a temperature of the molten glass-forming material 306 within the containment area 307 of the container 305. For example, a thermocouple 350 placed directly into the molten glass-forming material 306 may melt or rapidly corrode such that an operational life of the thermocouple 350 may be reduced and rendered impractical. In addition, a thermocouple 350 in a sheath (e.g. of platinum or platinum-containing alloy) placed directly into the molten glass-forming material 306 may also corrode relatively rapidly, particularly in the presence of metal (e.g., copper, iron, silver, platinum and/or other metal), such that an operational life of the thermocouple 350 and the sheath may be reduced and likewise rendered impractical.

As shown in FIGS. 3-7, embodiments of the disclosure protect the thermocouple 350 of the molten material apparatus 300 with a protective sleeve 320 mounted at least partially within the opening 315 of the wall 310 of the container 305. Advantageously, the protective sleeve 320 can protect a thermocouple 350 from exposure to the molten glass-forming material 306 thus, for example, extending an operational life of the thermocouple 350. The protective sleeve 320 can be fabricated from a wide range of refractory ceramic materials. In one embodiment, the refractory ceramic material can include a chemical compound selected from the group consisting of tin oxide, chrome oxide, and fused zirconia. For instance, the chemical compound may comprise any of the above compounds either alone or in any combination with one another. Such compounds can provide a desired resistance to corrosion with molten glass compositions including metal (e.g., copper, iron, silver, platinum and/or other metal). The refractory ceramic material can be compatible with the molten glass-forming material 306. For example, the refractory ceramic material of the protective sleeve 320 may reduce or prevent corrosion and/or failure of the protective sleeve 320 when exposed to the molten glass-forming material 306.

In some embodiments, the thermocouple 350 can include a platinum/rhodium alloy thermocouple 350. In other embodiments, the thermocouple 350 can include a type B thermocouple 350 that can measure temperatures within a range of from about 1600° C. to about 1700° C. without thermal damage while functioning within this temperature range. For purposes of this application, a type B thermocouple is a platinum/rhodium alloy thermocouple with a first conductor including a platinum/rhodium content of Pt/Rh 70%/30% and a second conductor including a platinum/rhodium content of Pt/Rh 94%/6%, by weight. It is to be understood that any type of thermocouple 350, including thermocouples not explicitly described herein, can be employed in further embodiments. The thermocouple 350 can measure a temperature of the molten glass-forming material 306 once, periodically, and continuously. In addition, the thermocouple 350 can communicate (e.g., wired communication, wireless communication) the measured temperature to a controller or other processor where the measured temperature to be recorded, manipulated, used in a calculation, used in a control system, etc. In some embodiments, the measured temperature can be provided to any one or more components of a glass manufacturing apparatus (e.g., glass manufacturing apparatus 101) to control an aspect of the glass manufacturing process.

Figure 4:
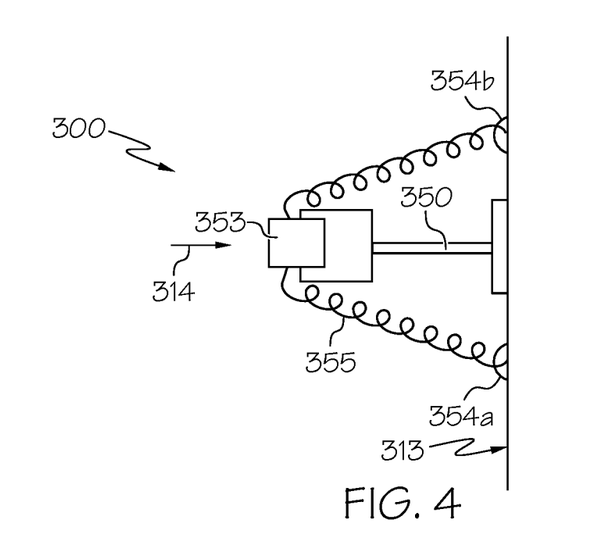
FIG. 4 illustrates a schematic view of an exemplary molten material apparatus along line 4-4 of FIG. 3.

As shown in FIG. 4, the thermocouple 350 can include a bracket 353 to which a spring 355 can connect to bias the thermocouple 350 in a direction 314 toward an interior of the container 305. For example, the spring 355 can attach to anchors 354a, 354b on an outer surface 313 of the wall 310 of the container 305 to bias the thermocouple 350 in the direction 314 toward the interior of the container 305. In further embodiments, the spring 355 can attach directly to the outer surface 313 of the wall 310 of the container 305. Still further, although illustrated with a single spring 355 with a central portion of the single spring 355 positioned within a cradle defined by the bracket 353, in other embodiments, separate or a plurality of springs may be provided. In addition, it will be appreciated that a wide range of biasing members may be provided to bias the thermocouple 350 in the direction 314. Indeed, in addition or alternatively to one or more springs, a biasing member may comprise a compression bracket, a tie down or other biasing member. Advantageously, biasing the thermocouple 350 can stabilize the thermocouple 350 from vibration and other movements during operation and can provide a contact force to maintain contact between the thermocouple 350 and a surface against which the thermocouple 350 can contact. For example, biasing the thermocouple 350 against a surface can improve the heat transfer between the material and the thermocouple 350 including any structure or material between the material and the thermocouple 350. Biasing the thermocouple 350 can therefore improve the quality of the measurement of the temperature of the material measured with the thermocouple 350. Furthermore, in some embodiments, biasing the thermocouple 350 may provide an alternative to permanently attaching the thermocouple 350 relative to the protective sleeve 320. As such, disassembly of the thermocouple from the protective sleeve 320 may be simplified to allow quick replacement of a protective sleeve 320 without damaging the thermocouple or requiring replacement of the thermocouple and/or the support sleeve.

Figure 5:
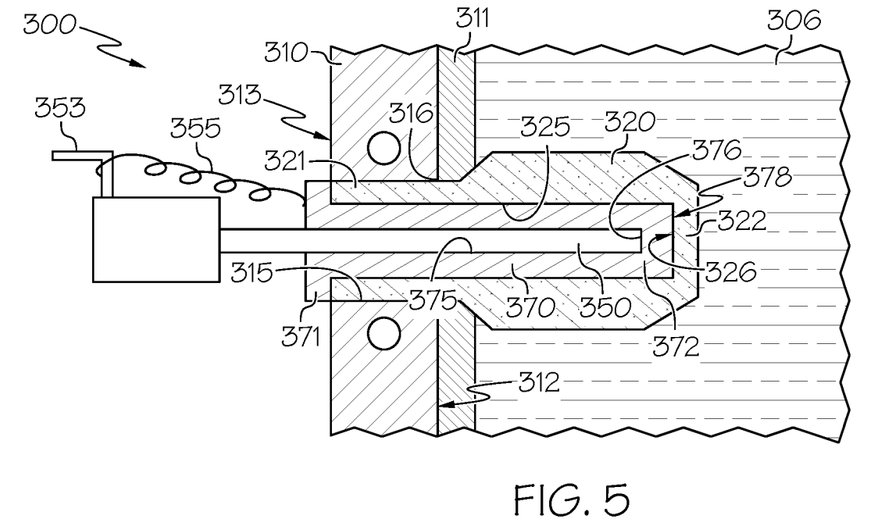
FIG. 5 illustrates an enlarged cross-sectional view of an exemplary molten material apparatus according to view 5 of FIG. 3.
Figure 6:
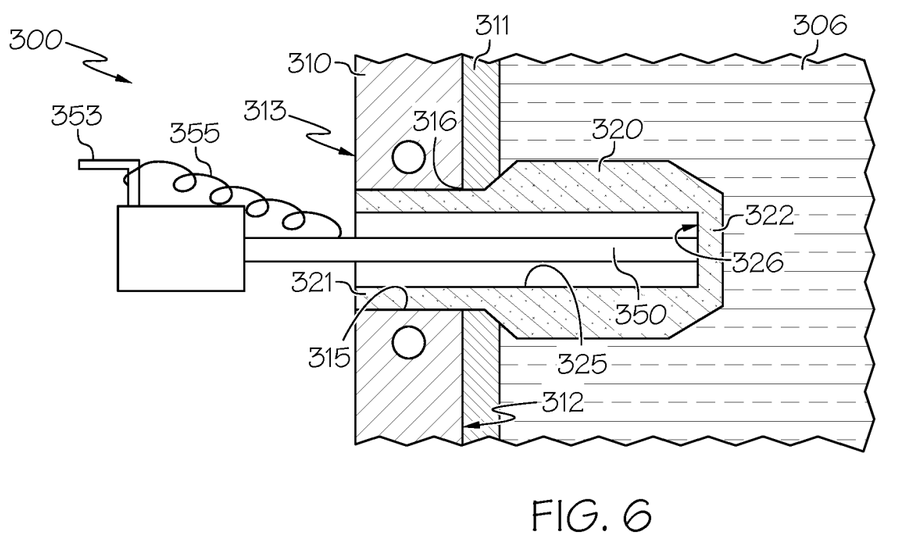
FIG. 6 illustrates an enlarged cross-sectional view of another exemplary molten material apparatus according to view 5 of FIG. 3.
Figure 7:
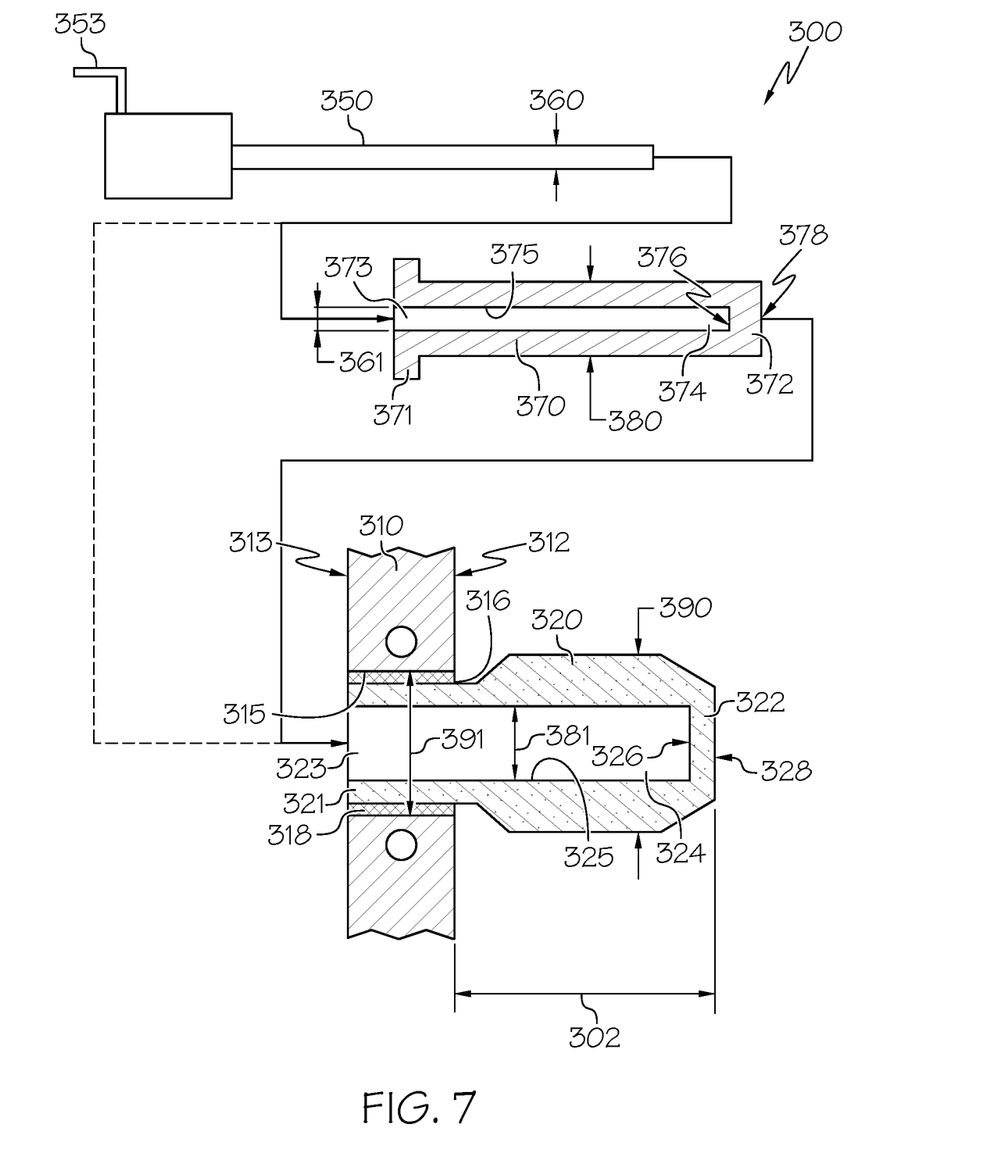
FIG. 7 illustrates a schematic assembly view of an exemplary molten material apparatus.

As illustrated in FIGS. 5-7, the protective sleeve 320 can include a protective sleeve first end portion 321, a protective sleeve second end portion 322 opposite the protective sleeve first end portion 321, and a protective sleeve internal bore 325. Throughout the application "internal bore" is intended to mean an internal passage, in internal channel, and internal opening, an internal conduit, an internal slot or other internal bore that may be produced by a boring procedure or produced by molding, grinding or other forming techniques not considered a boring procedure. The protective sleeve internal bore 325 can include a protective sleeve open end 323 (see FIG. 7) at the protective sleeve first end portion 321 and a protective sleeve closed end 324 at the protective sleeve second end portion 322. The protective sleeve closed end 324 can be defined by a protective sleeve inner end surface 326 of the protective sleeve second end portion 322.

In some embodiments, the molten material apparatus 300 can optionally include a support sleeve 370 at least partially positioned within the protective sleeve internal bore 325 of the protective sleeve 320. The support sleeve 370 can include a support sleeve first end portion 371, a support sleeve second end portion 372 opposite the support sleeve first end portion 371, and a support sleeve internal bore 375. As shown in FIG. 7, the support sleeve internal bore 375 can include a support sleeve open end 373 at the support sleeve first end portion 371 and a support sleeve closed end 374 at the support sleeve second end portion 372. The support sleeve closed end 374 can be defined by a support sleeve inner end surface 376 of the support sleeve second end portion 372.

As shown in FIG. 7, the protective sleeve 320 can include a protective sleeve outer dimension 390 and a protective sleeve internal bore dimension 381. Furthermore, the support sleeve 370 can include a support sleeve outer dimension 380 and a support sleeve internal bore dimension 361. Similarly, the thermocouple 350 can include a thermocouple outer dimension 360. The support sleeve 370 can structurally support the protective sleeve 320, in some embodiments. For example, the support sleeve 370 can be manufactured from a material (e.g., metal) that includes a higher ductility compared to the relatively fragile material (e.g., refractory ceramic material) from which the protective sleeve 320 can be manufactured. In some embodiments, the support sleeve 370 can include a platinum or a platinum alloy that may resist high temperature environments and provide high thermal conductivity to increase the temperature measurement response time of the thermocouple 350. In other embodiments, the support sleeve 370 can include alternative materials that can withstand high temperatures including molybdenum, alumina, and other materials. Advantageously, the refractory ceramic material of the protective sleeve 320 can be more compatible with the corrosive molten glass-forming material 306 than the material of the support sleeve 370. At the same time, the support sleeve 370 may enhance the structural integrity of the protective sleeve 320. For instance, the support sleeve 370 may help the protective sleeve 320 resist chipping, cracking or other modes of failure resulting from applications where the protective sleeve 320 has features (e.g., material, size, shape) that renders the protective sleeve fragile or less capable of resisting operating stresses. Operating stresses, for example, can result from heating or cooling the protective sleeve, molten material currents impacting the protective sleeve, heating processes of the molten glass, etc.

As shown in FIG. 5, the protective sleeve internal bore dimension 381 can accommodate the support sleeve outer dimension 380, and the support sleeve internal bore dimension 361 can accommodate the thermocouple outer dimension 360 such that the thermocouple 350 can be positioned within the support sleeve internal bore 375 and the support sleeve 370 can be positioned within the protective sleeve internal bore 325. In some embodiments, the support sleeve 370 can fit snuggly within the protective sleeve internal bore 325. In other embodiments, the support sleeve outer dimension 380 can be less than the protective sleeve internal bore dimension 381 and a space can be provided between the support sleeve 370 and the protective sleeve internal bore 325. In other embodiments, the thermocouple outer dimension 360 can be less than the support sleeve internal bore dimension 361 and a space can be provided between the thermocouple 350 and the support sleeve internal bore 375. In some embodiments, the thermocouple 350 can fit snuggly within the support sleeve internal bore 375.

The removable nature of some embodiments where the support sleeve 370 can be removed from the protective sleeve 320 and or where the thermocouple 350 can be removed from the support sleeve 370 can allow easy inspection, repair or replacement of the protective sleeve 320, support sleeve 370 and/or the thermocouple 350. For example, after significant wear and use, the thermocouple 350 and the support sleeve 370, if provided, may be easily removed from the protective sleeve 320 to replace the protective sleeve 320 with a new protective sleeve 320 without discarding other expensive components (e.g., the thermocouple 350 and/or the optional support sleeve 370).

In other embodiments, as shown in FIG. 6, the protective sleeve internal bore dimension 381 can accommodate the thermocouple outer dimension 360 such that the thermocouple 350 can be positioned within the protective sleeve 320 (e.g., without the support sleeve 370). In some embodiments, the thermocouple 350 can fit snuggly within the protective sleeve internal bore 325. In other embodiments, the thermocouple outer dimension 360 can be less than the protective sleeve internal bore dimension 381 and a space can be provided between the thermocouple 350 and the protective sleeve internal bore 325. Accordingly, the thermocouple 350 can be removed from the protective sleeve 320 to, for example, inspect the thermocouple 350, repair the thermocouple 350, or replace the thermocouple 350. Furthermore, as stated above, the thermocouple may also be removed to allow inspection, repair or replacement of the protective sleeve 320 while allowing reuse of the thermocouple. The protective sleeve 320 may be provided without the support sleeve 370 in embodiments where the protective sleeve 320 is sufficiently strong to resist processing stresses without being strengthened by the support sleeve 370.

As shown in FIG. 6, the thermocouple 350 can be positioned within the protective sleeve internal bore 325 of the protective sleeve 320, and the thermocouple 350 can contact the protective sleeve inner end surface 326 of the protective sleeve second end portion 322. In further embodiments, the thermocouple 350 can be biased towards the protective sleeve inner end surface 326 of the protective sleeve second end portion 322 (e.g., by spring 355). In some embodiment, as shown in FIG. 5, the thermocouple 350 can be positioned within the support sleeve internal bore 375 of the support sleeve 370, and the thermocouple 350 can contact the support sleeve inner end surface 376 of the support sleeve second end portion 372. In further embodiments, the thermocouple 350 can be biased against the support sleeve inner end surface 376 of the support sleeve second end portion 372 (e.g., by spring 355). In addition, a support sleeve outer end surface 378 of the support sleeve second end portion 372 can be biased against and contact the protective sleeve inner end surface 326 of the protective sleeve second end portion 322 (e.g., by spring 355).

As illustrated in FIG. 7, the protective sleeve 320 can be secured within the opening 315 of the wall 310 with a bonding agent 318 (e.g., cement, glue, sealant, etc.) at the interface 316 between the wall 310 of the container 305 and the protective sleeve 320. Referring back to FIGS. 3, 5, and 6, for example, in some embodiments, solid glass 311 can seal an interface 316 between the wall 310 of the container 305 and the protective sleeve 320. The solid glass 311 and the bonding agent 318 can, either alone or in combination, seal the interface 316 between the wall 310 of the container 305 and the protective sleeve 320. Accordingly, the protective sleeve 320 can be removed from the opening 315 in the wall 310 to, for example, inspect the protective sleeve 320, repair the protective sleeve 320, or replace the protective sleeve 320. Removal of the protective sleeve 320 from the opening 315 in the wall 310 can be accomplished by separating the protective sleeve 320 from the wall 310 at the interface 316. For example, the bonding agent 318 and/or the solid glass 311 at the interface 316 can be removed (e.g., chiseled, broken, etc.) to separate the protective sleeve 320 from the wall 310 of the container 305.

As further shown in FIG. 7, the opening 315 can include an opening dimension 391 into which the protective sleeve 320 can be inserted. In some embodiments, the protective sleeve outer dimension 390 can be larger than the opening dimension 391 of the opening 315 in the wall 310 of the container 305. In further embodiments, the protective sleeve outer dimension 390 can be about the same as the opening dimension 391 of the opening 315 in the wall 310 of the container 305. It is to be understood that the larger the protective sleeve outer dimension 390, the more protection the protective sleeve 320 can provide the thermocouple 350 and the more the protective sleeve 320 can be strengthened to resist damage in use. Conversely, the smaller the protective sleeve outer dimension 390, the better (e.g., faster) heat can transfer from the molten glass-forming material 306 through the protective sleeve 320 to the thermocouple 350. Accordingly, in some embodiments, the protective sleeve outer dimension 390 can be chosen based at least in part on a trade-off between a rate of heat transfer through the protective sleeve 320 and a level of protection of the protective sleeve 320.

In some embodiments, the protective sleeve 320 can extend within the containment area 307 by a distance 302 of from greater than 0 cm to about 25 cm from an inner surface 312 of the wall 310 of the container 305. In further embodiments, the distance 302 can be from greater than 0 cm to about 15 cm. In another, the distance 302 can be from about 2 cm to about 15 cm. In still another embodiment, the distance 302 can be from about 2 cm to about 7 cm. In yet another embodiment, the distance 302 can be from about 3 cm to about 5 cm. The distance 302 can be based at least in part on a location at which a temperature of the molten glass-forming material 306 is to be measured. For example, is some embodiments (not shown), a protective sleeve outer end surface 328 of the protective sleeve 320 can be flush with the inner surface 312 of the wall 310 and the layer of solid glass 311 can extend over the protective sleeve outer end surface 328 and the thermocouple 350 can measure a temperature corresponding to a temperature of the solid glass 311 at the inner surface 312 of the wall 310. In other embodiments, for example as shown in FIGS. 3, 5, and 6, the protective sleeve 320 can extend into the molten glass-forming material 306 and the thermocouple 350 can measure a temperature corresponding to a temperature of the molten glass-forming material 306 at a distance 302 from the inner surface 312 of the wall 310 of the container 305.

In some embodiments, a method of processing molten material 121 can include inserting the thermocouple 350 into the protective sleeve 320 and measuring a temperature of material (e.g., molten glass-forming material 306) within the containment area 307 of the container 305 with the thermocouple 350. In some embodiments, the method can include solidifying a quantity of the molten glass-forming material 306 into a layer of solid glass 311 lining an inner surface 312 of the wall 310 of the container 305 by cooling the wall 310 of the container 305 with liquid 303. For example, liquid 303 can circulate through the wall 310 in an internal liquid path 304. In some embodiments, the method can include solidifying a quantity of the molten glass-forming material 306 into a solid glass 311 that seals an interface 316 between the wall 310 of the container 305 and the protective sleeve 320.

In some embodiments, the protective sleeve second end portion 322 of the protective sleeve 320 can pass through the opening 315 of the wall 310 and through the layer of solid glass 311 such that the protective sleeve second end portion 322 is positioned within the molten glass-forming material 306. In some embodiments, the method can include supporting the protective sleeve 320 by inserting the support sleeve 370 at least partially within the protective sleeve internal bore 325 of the protective sleeve 320.

In some embodiments, measuring the temperature of material (e.g., molten glass-forming material 306) can include biasing the thermocouple 350 against the protective sleeve inner end surface 326 of the protective sleeve 320. In some embodiments, measuring the temperature of the material can include biasing the thermocouple 350 against the support sleeve inner end surface 376 of the support sleeve closed end 374 portion such that the support sleeve outer end surface 378 of the support sleeve second end portion 372 is biased against and thereby contacts the protective sleeve inner end surface 326 of the protective sleeve 320.

It will be appreciated that the various disclosed embodiments may involve particular features, elements or steps that are described in connection with that particular embodiment. It will also be appreciated that a particular feature, element or step, although described in relation to one particular embodiment, may be interchanged or combined with alternate embodiments in various non-illustrated combinations or permutations.

It is to be understood that, as used herein the terms "the," "a," or "an," mean "at least one," and should not be limited to "only one" unless explicitly indicated to the contrary. Thus, for example, reference to "a component" includes embodiments having two or more such components unless the context clearly indicates otherwise.

Ranges can be expressed herein as from "about" one particular value, and/or to "about" another particular value. When such a range is expressed, embodiments include from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that any particular order be inferred.

While various features, elements or steps of particular embodiments may be disclosed using the transitional phrase "comprising," it is to be understood that alternative embodiments, including those that may be described using the transitional phrases "consisting" or "consisting essentially of," are implied. Thus, for example, implied alternative embodiments to an apparatus that comprises A+B+C include embodiments where an apparatus consists of A+B+C and embodiments where an apparatus consists essentially of A+B+C.

It will be apparent to those skilled in the art that various modifications and variations can be made to the present disclosure without departing from the spirit and scope of the application. Thus, it is intended that the present application cover the modifications and variations of this disclosure provided they come within the scope of the appended claims and their equivalents.

What is claimed is:

1. A molten material apparatus comprising:
   a container including a wall at least partially defining a containment area and an opening extending through the wall;
   a protective sleeve mounted at least partially within the opening of the wall of the container, the protective sleeve including a first end portion, a second end portion opposite the first end portion, and an internal bore including an open end at the first end portion and a closed end defined by an inner end surface of the second end portion;
   a thermocouple positioned within the internal bore of the protective sleeve and biased towards the inner end surface of the second end portion; and
   a layer of solid glass lining an inner surface of the wall of the container, wherein the solid glass seals an interface between the wall of the container and the protective sleeve;
   wherein the wall of the container comprises one or more internal liquid paths operable to cool the wall of the container through the circulation of a liquid.

2. The molten material apparatus of claim 1, wherein the protective sleeve is fabricated from a refractory ceramic material.

3. The molten material apparatus of claim 2, wherein the refractory ceramic material includes a chemical compound selected from the group consisting of: tin oxide, chrome oxide, and fused zirconia.

4. The molten material apparatus of claim 1, wherein the thermocouple comprises a platinum/rhodium alloy thermocouple.

5. The molten material apparatus of claim 4, wherein the thermocouple comprises a type B thermocouple.

6. The molten material apparatus of claim 1, wherein the thermocouple contacts the inner end surface of the second end portion.

7. The molten material apparatus of claim 1, further comprising a support sleeve at least partially positioned within the internal bore of the protective sleeve, the support sleeve including a first end portion, a second end portion opposite the first end portion of the support sleeve, and an internal bore including an open end at the first end portion of the support sleeve.

8. The molten material apparatus of claim 7, wherein the internal bore of the support sleeve further includes a closed end defined by an inner end surface of the second end portion of the support sleeve, and the thermocouple is positioned within the internal bore of the support sleeve and biased against the inner end surface of the second end portion of the support sleeve.

9. The molten material apparatus of claim 8, wherein an outer end surface of the second end portion of the support sleeve is biased against the inner end surface of the second end portion of the protective sleeve.

10. The molten material apparatus of claim 7, wherein the support sleeve comprises a platinum or a platinum alloy.

11. The molten material apparatus of claim 1, wherein the protective sleeve extends within the containment area by a distance of from greater than 0 cm to about 25 cm from an inner surface of the wall of the container.

12. The molten material apparatus of claim 1, further comprising molten glass-forming material within the containment area of the container.

13. The molten material apparatus of claim 12, wherein the molten glass-forming material comprises metal.

14. The molten material apparatus of claim 12, wherein the layer of solid glass separates the container from the molten glass-forming material.

15. A molten material apparatus comprising:
    a container including a wall at least partially defining a containment area and an opening extending through the wall;
    a protective sleeve mounted at least partially within the opening of the wall of the container, wherein the protective sleeve is fabricated from a refractory ceramic material that includes a chemical compound selected from the group consisting of: tin oxide, chrome oxide, and fused zirconia;
    a thermocouple positioned within an internal bore of the protective sleeve; and
    a layer of solid glass lining an inner surface of the wall of the container, wherein the solid glass seals an interface between the wall of the container and the protective sleeve;
    wherein the wall of the container comprises one or more internal liquid paths operable to cool the wall of the container through the circulation of a liquid.

16. The molten material apparatus of claim 15, wherein the thermocouple comprises a platinum/rhodium alloy thermocouple.

17. The molten material apparatus of claim 16, wherein the thermocouple comprises a type B thermocouple.

18. The molten material apparatus of claim 15, wherein the thermocouple contacts an inner end surface of the protective sleeve that at least partially defines the internal bore.

19. The molten material apparatus of claim 15, further comprising a support sleeve at least partially positioned within the internal bore of the protective sleeve.

20. The molten material apparatus of claim 19, wherein the thermocouple is positioned within an internal bore of the support sleeve.

21. The molten material apparatus of claim 20, wherein the thermocouple contacts an inner end surface of the support sleeve that defines a closed end of the internal bore of the support sleeve, and an outer end surface of the support sleeve contacts an inner end surface of the protective sleeve that at least partially defines the internal bore of the protective sleeve.

22. The molten material apparatus of claim 19, wherein the support sleeve comprises a platinum or a platinum alloy.

23. The molten material apparatus of claim 15, wherein the protective sleeve extends within the containment area by a distance of from greater than 0 cm to about 25 cm from an inner surface of the wall of the container.

24. The molten material apparatus of claim 15, further comprising molten glass-forming material within the containment area of the container.

25. The molten material apparatus of claim 24, wherein the molten glass-forming material comprises metal.

* * * * *

UNITED STATES PATENT AND TRADEMARK OFFICE
CERTIFICATE OF CORRECTION

Page 1 of 1

PATENT NO. : 10,656,024 B2
APPLICATION NO. : 15/091183
DATED : May 19, 2020
INVENTOR(S) : Curtis Richard Cowles et al.

It is certified that error appears in the above-identified patent and that said Letters Patent is hereby corrected as shown below:

In the Claims

In Column 13, Line 31, Claim 1, delete "dosed" and insert -- closed --, therefor.

Signed and Sealed this
Twentieth Day of July, 2021

Drew Hirshfeld
*Performing the Functions and Duties of the
Under Secretary of Commerce for Intellectual Property and
Director of the United States Patent and Trademark Office*